United States Patent [19]

LaMarre et al.

[11] Patent Number: 4,661,518

[45] Date of Patent: Apr. 28, 1987

[54] SYNERGISTIC BIOCIDE OF 2-(P-HYDROXYPHENOL)-GLYOXYLOHYDROXIMOYL CHLORIDE AND 2,2-DIBROMO-3-NITRILOPROPIONAMIDE

[75] Inventors: Thomas M. LaMarre, Aurora; Cynthia H. Martin, Plainfield, both of Ill.

[73] Assignee: Nalco Chemical Company, Naperville, Ill.

[21] Appl. No.: 874,911

[22] Filed: Jun. 16, 1986

[51] Int. Cl.$^4$ .................. A01N 33/24; A01N 37/34
[52] U.S. Cl. .................. 514/528; 210/764; 514/640
[58] Field of Search .................. 514/528, 640

[56] References Cited

U.S. PATENT DOCUMENTS 3,929,562  12/1975  Sheara et al. .................. 514/372

OTHER PUBLICATIONS

C.A.; vol. 92 (1980), 92:127,066f.
Applied Microbiology, by S. C. Kull et al., vol. 9, pp. 538–541, (1936), "Mixtures of Quaternary Ammonium Compounds & Long-Chain Fatty Acids as Antifungal Agents".

Primary Examiner—Allen J. Robinson
Attorney, Agent, or Firm—John G. Premo; Anthony L. Cupoli; Donald G. Epple

[57] ABSTRACT

The invention comprises a biocidal composition useful in treating industrial process waters to prevent and control the growth of gram-negative bacteria, which composition contains a synergistic mixture of 2-(p-hydroxyphenol) glyoxylohydroxymoyl chloride and 2,2-dibromo-3-nitrilopropionamide.

2 Claims, No Drawings

SYNERGISTIC BIOCIDE OF 2-(P-HYDROXYPHENOL)-GLYOXYLOHYDROXIMOYL CHLORIDE AND 2,2-DIBROMO-3-NITRILOPROPIONAMIDE

INTRODUCTION

The present invention relates to certain processes and compositions useful for inhibiting the growth of slime in water employed for industrial purposes, particularly water employed in the manufacture of pulp and paper, water employed in cooling water systems, as well as other industrial waters. The novel compositions and methods of the present invention are processes or mixtures which show unexpected synergistic activity against bacteria and fungi which are common to the above mentioned industrial waters and which produce slimes in aqueous systems or bodies, which slimes are objectionable from either an operational or aesthetic point of view. Specifically, the invention is directed to the use of compositions comprising a combination of 2-(Phydroxyphenol)-glyoxylohydroximoyl chloride (i.e. HGHMCL)-3-nitrilopropionamide (i.e. DBNPA).

The mechanisms by which chemical agents exert antimicrobial activity depend upon the effective contact between the chemical and the organism, and involve disruptive interactions with some biochemical or physical component of the organism, which component is essential to its structure or metabolism. The targets may be an enzyme, or enzymes, the cell membrane, an intracellular system, the cytoplasm, or any combination of these. The nature of the action of the toxicant is dependent on the organism, on the antimicrobial agent, and on the environment in whch the interaction occurs. The unique composition of each toxicant implies a differrent mode of action.

The present invention provides superior antimicrobial activity through a synergy in which the disruptive interaction on the organism by the two toxicants together is greater than the sum of both toxicants taken alone. The synergy does not arise from the expected activity of the components or from a predictable improvement in activity. In all caes, the synergism depends largely on- the interactions of the antimicrobial agents with the organism. The cellular processes are so complex as to render such synergism and unpredictable, and indeed rare, phenomenon.

THE INVENTION

The invention comprises a biocidal composition useful in treating industrial process waters to prevent and control the growth of gram-negative bacteria, which composition comprises a synergistic mixture of: 2-(p-hydroxyphenol)-glyoxylohydroximoyl chloride and 2,2-dibromo-3-nitrilopropionamide.

In a preferred embodiment of the invention, 2-(p-hydroxyphenol)-glyoxylohydroximoyl chloride is combined with 2,2-dibromo-3-nitrilopropionamide to provide weight ratios ranging from between 10–90% by weight to 90–10% by weight.

This combination is effective at low dosages, e.g. 1–10 ppm.

The troublesome slimeforming bacteria in industrial process waters tend to be primarily gram-negative rod-shaped aerobes. Of this group, *Pseudomonas aeruginosa* is one of the most common and most difficult to control. The invention is capable of affording good control of *Pseudomonas aeruginosa*. It is also capable of affording control of other species of bacteria, in particular other species of gram-negative, rod-shaped aerobes of such genera as Aerobacter, Flavobacterium, Pseudomonas, for example, *Pesudomonas aeruginosa, Pseudomonas fluorescens, Pseudomonas levanicum, Pseudomonas stutzeri, Pseudomonas maltophilia, Aerobacter aerogenes, Aerobacter cloacae,* and others.

The combination of toxicants here presented has greater activity than either constituent alone. The combination of toxicants incurs a broader spectrum of activity: the combination is widely effective against bacteria and has a greater range of effective pH.

While the synergism will be shown to exist over the wide range mentioned above, in the case of bacteria, and particularly Pseudomonas bacteria, preferred weight ratios of HGHMCL/DBNPA are:
10/90
75/25
25/75
50/50

Test Method

The procedure is as follows:

The synergism of these components is demonstrated by adding 2-(p-hydroxyphenyl)glyoxylohydroximoyl chloride (HGHMCl) and 2,2-dibromo-3-nitrilopropionamide (DBNPA) in varying ratios over a range of concentrations to sterile white water from a paper mill. The white water, adjusted to the desired pH, was inoculated with *Pseudomonas aeruginosa*, ATCC 15442.

The total count of the control was $9.0 \times 10^7$ bacteria per milliliter. The concentrations of the above toxicants were added to aliquots of the inoculated white water, and these aliquots were incubated at 37° C. for 24 hours. In this study of the control of bacterial growth, the nutrient medium for plating was tryptone glucose extract agar, poured at 50° C. into sterile Petri dishes containing the appropriate dilutions of the white water which had been inoculated and treated as described. Once the medium in these dilution plates had solidified, the plates were incubated for over forty-eight hours at 37° C. After the incubation, the results were read as growth or no growth: the lowest concentration of each toxicant or of each ratio of the combined toxicants that prevented growth on the agar was taken as the end point. This procedure provides the toxicant with a greater challenge by testing the toxicant under conditions which approximate the conditions under which they will be used.

The end points of each of the ratios tested were compared with end points of the concentrations of the pure toxicants. Synergism was determined according to the industrially-accepted method described by S. C. Kull, P. C. Eisman, H. D. Sylwestrowicz, and R. L. Mayer in *Applied Microbiology,* Vol. 9, pages 538–541, (1936), which is herein included as reference.

As regards the Kull et al. document, the data here presented can be described as follows:

$Q_A$ = the ppm of actives of HGHMCl alone which produced an endpoint
$Q_a$ = the ppm of actives of HGHMCl, in combination, which produced an endpoint
$Q_B$ = the ppm of actives of DBNPA alone which produced an endpoint
$Q_b$ = the ppm of actives of DBNPA, in combination, which produced an endpoint -continued if $\dfrac{Q_a}{Q_A} + \dfrac{Q_b}{Q_B}$     <1 indicates synergy
    >1 indicates antagonism
    =1 indicates additivity Ratios of HGHMCl/DBNPA: 100/0, 0/100, 90/10, 10/90, 75/25, 25/75, 50/50.

Concentrations tested for each ratio in terms of parts per million of actives: 0.3, 0.6, 1.0, 1.5, 3.0, 5.0, 7.5, 10, 20, 30, 40, 50, 60, 70, 80, 90, 100, 110, 120.

The above test method is reproduceable and is a good method for determining the range of synergism existing against candidate biocides being screened for application in the treatment of biologically contaminated industrial waters. The efficacy and validity of this test method is discussed in the Appendix which appears hereafter. For purposes of simplification of test results presented hereafter, the Appendix also contains the calculations used to produce the test results set forth in Table I. The effectiveness of the combination of HGHMCl/DBNPA is set forth below in Table I.

TABLE I

SYNERGISM STUDY FOR COMBINATION BIOCIDES AGAINST BACTERIA

Growth: +
No Growth: −
Control Culture: 9. × $10^7$ organisms per ml

| Ratio (HGHMCl/ DBNPA) | Concentrations (ppm) | | | | | | | | | | | | |
|---|---|---|---|---|---|---|---|---|---|---|---|---|---|
| | .3 | .6 | 1.0 | 1.5 | 3.0 | 5.0 | 7.5 | 10 | 20 | 30 | 40 | 50 | 60 |
| 100/0 | + | + | + | + | + | + | − | − | − | − | − | − | − |
| 0/100 | + | + | + | + | + | + | + | + | − | − | − | − | − |
| 90/10 | + | + | + | + | + | − | − | − | − | − | − | − | − |
| 10/90 | + | + | + | + | − | − | − | − | − | − | − | − | − |
| 75/25 | + | + | + | + | − | − | − | − | − | − | − | − | − |
| 25/75 | + | + | + | + | − | − | − | − | − | − | − | − | − |
| 50/50 | + | + | + | + | − | − | − | − | − | − | − | − | − |

| Ratio | $\dfrac{Qa}{QA} + \dfrac{Qb}{QB}$ | Rating |
|---|---|---|
| 90/10 | 0.938 | <1 Synergy or additive |
| 10/90 | 0.175 | <1 Synergy |
| 75/25 | 0.338 | <1 Synergy |
| 25/75 | 0.213 | <1 Synergy |
| 50/50 | 0.275 | <1 Synergy |

ANTAGONISTIC COMBINATIONS

The two components of the present invention were tested singly with a variety of other toxicants, using the methods described above; as is expected, most such combinations are antagonistic or merely additive. Three such examples are presented below in order to better show the nature of such testing.

First, tributyl tetradecyl phosphonium chloride (TTPC) was found to be antagonistic in combination with 2,2-dibromo-3-nitrilopropionamide (DBNPA), in a test against bacteria.

| Ratio TTPC/DBNPA | Endpoint (ppm actives) | $\dfrac{Qa}{QA} + \dfrac{Qb}{QB}$ | Rating |
|---|---|---|---|
| 100/0 | 30.0 | 1.00 | |
| 0/100 | 0.6 | 1.00 | |
| 90/10 | 7.5 | 1.48 | Antagonistic |
| 10/90 | 1.0 | 1.53 | Antagonistic |
| 75/25 | 5.0 | 2.21 | Antagonistic |
| 25/75 | 1.0 | 1.26 | Antagonistic |
| 50/50 | 1.5 | 1.28 | Antagonistic |

Second, 2-(p-hydroxyphenol)-glyoxylohydroximoyl chloride (HGHMCl) was found to be antagonistic in combination with a blend of quaternary amines (QUAT), in a test against bacteria.

| Ratio HGHNCl/QUAT | Endpoint (ppm actives) | $\dfrac{Qa}{QA} + \dfrac{Qb}{QB}$ | Rating |
|---|---|---|---|
| 100/0 | 20 | 1.00 | |
| 0/100 | 30 | 1.00 | |
| 90/10 | 40 | 1.93 | Antagonistic |
| 10/90 | 20 | 0.70 | Synergistic |
| 75/25 | 60 | 2.75 | Antagonistic |
| 25/75 | 30 | 1.13 | Antagonistic |
| 50/50 | 70 | 2.92 | Antagonistic |

Third, 1,5-pentanedial (PD) was also found to be antagonistic in combination with 2,2-bromo-3-nitrilopropionamide (DBNPA), when tested against bacteria.

| Ratio PD/DBNPA | Endpoint (ppm actives) | $\dfrac{Qa}{QA} + \dfrac{Qb}{QB}$ | Rating |
|---|---|---|---|
| 100/0 | 100 | 1.00 | |
| 0/100 | 40 | 1.00 | |
| 90/10 | 90 | 1.04 | Additive |
| 10/90 | 90 | 2.12 | Antagonistic |
| 75/25 | >100 | >1.38 | Antagonistic |
| 25/75 | 60 | 1.28 | Antagonistic |
| 50/50 | 90 | 1.58 | Antagonistic |

APPENDIX

Discussion

The conventional presentation of a test of synergy demands that the data be presented in terms of growth or no growth. The convention has the merit of presenting the data simply and directly in terms that make the calculation of synergy straightforward. This presentation may, however, require a thorough explanation of the factors which are taken into account in the determination of the endpoints of the test. The determination of synergy depends wholly on these endpoints.

The data presented in Table I demonstrate synergy, but may require explanation. First, the indication of growth (+) in Table I is heavy growth. No growth (−) indicates no growth on a zero-dilution plate, on a one-dilution plate, and on a two dilution plate. The zero-dilution plate will show as few as one bacterial colony per milliliter; the lowest count on one-dilution plate is ten bacteria per milliliter, and the two-dilution plate shows a bacterial count greater than $10^2$ bacteria per milliliter. In short, in Table I, the difference between growth (+) and no growth (−) involves a three-log reduction in bacterial count. For example, in the case of the ratio 100/0, the bacterial count at a concentration of 5 ppm was greater than $10^2$ bacteria per milliliter. At 7.5 ppm, the bacterial count was below detection (less than 1 bacteria per milliliter). Therefore, the endpoint for 100/0 is taken to be 7.5 ppm.

The endpoint for 100/0 is, in the strictest sense, between 5 and 7.5 ppm. In this case, where a concentration of toxicant as high as 5 ppm is not capable of completely inhibiting growth, a three-log reduction in bacterial count is not to be expected by increasing the concentration of biocide by less than 2–3 ppm.

The endpoint cannot fall closer to 5 ppm than to 7.5 ppm. The 2.5 ppm interval is indeed significant when testing toxicants with this magnitude of toxicity. Additional data points at closer intervals are unnecessary. The progression of the increments between concentrations in these experiments (0.3, 0.6, 1.0, 1.5, 3.0, 5.0, 7.5, 10, 20 . . . etc.) is standard method in producing representative microbiological data.

The same logic applies to all the endpoints of the test. The best and worst extropolations of the data can be determined in this way. Since the endpoints of 100/0 must fall closer to 7.5 than to 5 ppm, and the endpoint of 0/100 must fall closer to 20 than to 10 ppm, let us say that;

$6.25 < QA < 7.5$ $15 < QB < 20$

Let us use the ratio 75/25 in this example because it is the least synergistic of the synergistic ratios. For the reasons described above, the endpoint for 75/25 must fall closer to 3 than to 1.5, therefore;

$$2.25 < 75/25 < 3$$

In the worst possible case;

$$QA = 6.25$$

$$QB = 15$$

And the worst endpoint for 75/25 under these circumstances is 3 ppm. Therefore, $$Qa = 0.75 \times 3 = 2.25$$

$$Qb = 0.25 \times 3 = 0.75$$

The formula for the calculation of synergy is defined to be;

$$(Qa)/(QA) + (Qb)/(QB) = 0.410$$

This formula shows the extent to which the combination of the two toxicants creates a surprising increase in activity. When the synergy ratio is less than 1, the combination is truly synergistic instead of antagonistic or merely additive. In this experiment, calculating the worst possible case for the least effective ratio, the ratio is still extremely synergistic.

In the test of synergy against bacteria, the endpoints are clearly defined, and generally the increase in activity presented by the combinations is well within the defined limits of synergistic activity. The ratio, 90/10, is within the defined limits of synergistic activity and probably but not definitely synergistic.

This presentation of the data goes to show how truly representative the endpoints are. The data, as presented and calculated in Table I, are not extrapolated into the best or worst cases. Instead, the data summarize the activity shown using standard method. As mentioned above, this interpretation also depends on understanding that the difference between growth and no growth in the synergy study against bacteria involves a three-log reduction in bacterial count. These interpretations of the data confirm that the ratios of toxicants, 10/90 through 75/25, result in an unexpected amelioration of toxicity.

| Calculations for Table I | |
|---|---|
| Calculations | |
| $Q_A$ = 7.5 ppm active<br>$Q_B$ = 20 ppm active | $\dfrac{Q_a}{Q_A} + \dfrac{Q_b}{Q_B} < 1$ = Synergy |
| A. 90/10<br>$Q_a$ = 7.5 ppm × .90 = 6.75<br>$Q_b$ = 7.5 ppm × .10 = .75<br>$\dfrac{6.75}{7.5} + \dfrac{.75}{20} = 0.938$ | B. 10/90<br>$Q_a$ = 3 ppm × .10 = .3<br>$Q_b$ = 3 ppm × .90 = 2.7<br>$\dfrac{.3}{7.5} + \dfrac{2.7}{20} = 0.175$ |
| C. 75/25<br>$Q_a$ = 3 ppm × 0.75 = 2.25<br>$Q_b$ = 3 ppm × 0.25 = .75<br>$\dfrac{2.25}{7.5} + \dfrac{.75}{20} = 0.338$ | D. 25/75<br>$Q_a$ = 3 ppm × 0.25 = .75<br>$Q_b$ = 3 ppm × 0.75 = 2.25<br>$\dfrac{.75}{7.5} + \dfrac{2.25}{20} = 0.213$ |
| E. 50/50<br>$Q_a$ = 3 ppm × 0.50 = 1.5<br>$Q_b$ = 3 ppm × 0.50 = 1.5<br>$\dfrac{1.5}{7.5} + \dfrac{1.5}{20} = 0.275$ | |

Having thus described the invention, it is claimed as follows:

1. A biological composition useful in treating industrial process waters to prevent and control the growth of gram-negative bacteria, which composition comprises a synergistic mixture which contains:
   a. from 0–75% by weight of 2-(p-hydroxyphenol)-glyoxylohydroxymoyl chloride; and
   b. from 90–25% by weight of 2,2-dibromo-3-nitrilopropionamide.

2. A biocidal composition useful in treating industrial process waters to prevent and control the growth of Pseudomonas bacteria, which composition comprises a synergistic mixture which contains:
   a. from 10–75% by weight of 2-(p-hydroxyphenol)-glyoxylohydroxymoyl chloride, and
   b. from 90–25% by weight of 2,2-dibromo-3-nitrilopropionamide.

* * * * *